United States Patent [19]

Gravenstein et al.

[11] Patent Number: 5,101,825
[45] Date of Patent: Apr. 7, 1992

[54] METHOD FOR NONINVASIVE INTERMITTENT AND/OR CONTINUOUS HEMOGLOBIN, ARTERIAL OXYGEN CONTENT, AND HEMATOCRIT DETERMINATION

[75] Inventors: Dietrich Gravenstein, Gainesville, Fla.; J. E. W. Beneken, Helmond, Netherlands; Samsun Lampotang, Gainesville, Fla.; Nikolaus Gravenstein, Gainesville, Fla.; Michael A. Brooks, Gainesville, Fla.; Gordon L. Gibby, Gainesville, Fla.; Robert J. Atwater, Gainesville, Fla.

[73] Assignee: BlackBox, Inc., Gainesville, Fla.

[21] Appl. No.: 368,636

[22] Filed: Jun. 20, 1989

Related U.S. Application Data

[63] Continuation-in-part of Ser. No. 264,119, Oct. 28, 1988, abandoned.

[51] Int. Cl.$^5$ ............................................. A61B 5/00
[52] U.S. Cl. ................................. 128/633; 128/637; 128/664; 128/898
[58] Field of Search ............... 128/633, 634, 665, 664, 128/898, 637; 606/10, 11, 13

[56] References Cited

U.S. PATENT DOCUMENTS

4,167,331  9/1979  Nielsen .
4,704,029  11/1987 Van Heuvelen ............... 128/633
4,805,623  2/1989  Jobsis ......................... 128/633

OTHER PUBLICATIONS

"A New Instrument for the Simultaneous Measurement of Total Hemoglobin, % Oxyhemoglobin, % Carboxyhemoglobin, % Methemoglobin, and Oxygen content in Whole Blood" by Brown; IEEE Trans. on Biomed. Eng., vol. BM627, No. 3, 3/80.

Donahoe, T. M., and R. L. Longini (1985) "A New Noninvasive Backscattering Oximeter," Proceeding of the IEEE 7th Annual Conference of the Engineering in Medicine and Biology Society, Sep. 27-30, 1985, vol. 1, IEEE (U.S.) 144-147.

Merrick, E. S., and T. J. Hayes (1976) "Continuous, Non-Invasive Measurements of Arterial Blood Oxygen Levels," Hewlett-Packard J. 28(2): 2-9.

*Primary Examiner*—David Shay
*Attorney, Agent, or Firm*—Saliwanchik & Saliwanchik

[57] ABSTRACT

Described here are a novel means and device for noninvasively quantifying important blood constituents. Total hemoglobin, arterial oxygen content, hematocrit, and other parameters can all be determined quickly and easily without the need for skin puncture or lengthy laboratory analysis. The invention described here concerns the simultaneous measurement of volume changes and changes in the mass of either oxyhemoglobin, total hemoglobin, or reduced hemoglobin. The data obtained by these measurements is used to quantify the parameters of interest.

14 Claims, 4 Drawing Sheets

(One dashed line is solid depending on algorithm followed)

METHOD FOR NONINVASIVE INTERMITTENT AND/OR CONTINUOUS HEMOGLOBIN, ARTERIAL OXYGEN CONTENT, AND HEMATOCRIT DETERMINATION

CROSS-REFERENCE TO A RELATED APPLICATION

This application is a continuation-in-part of our co-pending application Ser. No. 264,119, filed Oct. 28, 1988 now abandoned.

BACKGROUND OF THE INVENTION

Arterial oxygen content was once assessed relying only on physical signs and symptoms such as cyanosis, tachypnea, bradycardia, tachycardia, dyspnea, and shortness of breath. Today, devices exist which allow accurate and rapid quantitative measurement of arterial oxygen content. Partial pressure of oxygen (PO2) in blood, percent hematocrit (Hct), percent arterial hemoglobin saturation (SaO2), gram-percent total hemoglobin (THb), and arterial oxygen content (CaO2) are all readily available to the physician in modern hospitals.

Unfortunately, however, measurement of these variables has until recently always required an invasive arterial puncture or phlebotomy. Once the whole blood sample is obtained, analysis is accomplished using spectrophotometric and chemical means.

During the early 1970's the first pulse oximeter was introduced. This device permitted approximation of SaO2, termed SpO2, by nonivasive means. The design was subsequently improved upon and the current generation of pulse oximeters is now commonplace in the intensive care unit (ICU), emergency room (ER), operating room (OR), and recovery room (RR).

Pulse oximeter design is well documented. It utilizes two light-emitting diodes (LED). Each LED emits a specific wavelength of light that is transmitted through the tissues to a photodetector. These wavelengths are chosen to be around 660 nm (red spectrum) and around 940 nm (near-infrared spectrum) because of the absorbency characteristics of oxyhemoglobin (HbO2) and reduced hemoglobin (RHb). An electrical signal consisting of two components is generated by the photodetector receiving the LED emission. There is an invariant direct current (DC) component to the signal which represents ambient background light and transmission of light through invariant, that is, nonpulsatile tissues such as skin, bone, and, to a certain extent, veins. The second component of the signal is an alternating current (AC) which represents the varying transmission of light through the pulse-varying tissues, i.e., the arteries and capillaries. Both the AC and DC components are affected by altered LED light intensity. The AC signals must be corrected for inter-LED light intensity differences prior to their use for SpO2 calculation. A pulse oximeter does this by dividing each LED's AC signal by its corresponding DC signal to produce the "corrected AC signal." The ratio of the corrected AC signal at 660 nm to that at 940 nm is compared to a stored calibration curve that yields SpO2. Thus, to calculate SpO2, a pulse oximeter generates a corrected AC signal for both LED wavelengths.

At this time, determination of the other variables, such as methemoglobin (MetHb), Hct, THb, CaO2, continues to require arterial puncture or phlebotomy. Skin puncture procedures are painful to the patient, time consuming, and provide opportunities for infection. There is a great need for a rapid and accurate noninvasive means of assessing THb, CaO2, and Hct. Such an assessment means would enable the health care provider to quickly evaluate and follow a patient's circulating blood status. Questions of hemodilution during volume expansion in the field, ER, and OR would be rapidly answered. Hemoconcentration after blood transfusion, hemodialysis or bone marrow transplantation could be followed without repeated venipuncture. Furthermore, many "routine" screening phlebotomies to assess THb and Hct such as for preoperative laboratory studies in children and adults could be eliminated.

BRIEF SUMMARY OF THE INVENTION

The subject invention concerns a novel means and device for noninvasive determination of total hemoglobin, arterial oxygen content, and hematocrit. Advantageously, these determinations can e made intermittently and/or continuously. The novel procedure described here is painless and eliminates the need for skin punctures. It is cost effective because there is no need for needles, syringes, gloves, bandages, or skilled technicians. Advantageously, critical data can be obtained in seconds rather than minutes or hours.

The determination of the blood parameters of interest is accomplished by measuring the change in the mass of hemoglobin (HbO2, RHb, or THb) resulting from a measured change in volume of blood. Each of these two measurements can be made noninvasively. For example, the change of mass of hemoglobin species can be measured photometrically by passing light of appropriate wavelength(s) through a portion of the body. The attenuation of the light which can be detected by a photometer, is related to the amount of hemoglobin species in the blood being analyzed. When changes occur in the volume or hemoglobin species concentration of blood being analyzed, corresponding changes in the mass of hemoglobin species can be measured. There are several noninvasive means which can be used to measure changes in blood volume in the portion of the body being analyzed.

Once these measurements have been made, the blood parameters of interest can be readily calculated.

DETAILED DESCRIPTION OF THE INVENTION

Oxygen content in arterial blood can be calculated using the formula:

$$CaO2(ml\ O2/dl) = THb(g/dl) \times SaO2 \times 1.39(ml\ O2/g\ HbO2), \quad (1)$$

where SaO2 is a fraction (HbO2/THb). Oxyhemoglobin (HbO2) is the oxygen carrying species of THb and can be calculated, $$HbO2(g/dl) = THb \times SaO2. \qquad (2)$$

Substituting Equation (2) into Equation (1), $$CaO2(ml\ O2/dl) = HbO2(g/dl) \times 1.39(ml\ O2/g\ HbO2). \qquad (3)$$

It becomes apparent that oxygen content can be calculated if oxyhemoglobin is known. Therefore, if the mass of oxyhemoglobin molecules [mHbO2(g)] in a given volume [V(dl)] is known, the oxygen content of that volume can be determined. Stated another way, if a change in the mHbO2 can be measured along with the corresponding change in volume, oxygen content can be measured. This relationship can be written $$HbO2(g/dl) = [mHbO2_{t2} - mHbO2_{t1}]/[V_{t2} - V_{t1}], \qquad (4)$$

where subscripts t1 and t2 represent two points in time. This can be rewritten as $$HbO2 = \Delta mHbO2/\Delta V, \qquad (5)$$

where $\Delta mHbO2$ is the change in mass of the HbO2 species and $\Delta V$ is the measured corresponding change in volume. The value for $\Delta mHbO2$, if mHbO2 is measured directly, can be calculated using a signal generated by a pulse oximeter, for example.

mHbO2 can also be determined indirectly. Indirect determination requires accurate SpO2 and either RHb or THb values. SaO2 and SpO2 are known to be close to each other. If RHb and SpO2 are known, then $$RHb = THb \times [(100 - SpO2)/100], \qquad (6)$$

and solving for THb yields $$THb = (RHb \times 100)/(100 - SpO2). \qquad (7)$$

Substituting equation (7) into $$HbO2 = THb - RHb, \qquad (8)$$

one obtains:

$$HbO2 = [(RHb \times 100)/(100 - SpO2)] - RHb. \qquad (9)$$

If THb and SpO2 are measured, Equation (2) can be utilized for indirect mHbO2 determination.

The invention can be practiced utilizing Equations (4) and (5). These equations are clinically useful approximations of the pertinent biological phenomena to be measured by the subject invention. Additional terms can be added to Equations (4) and (5). These additional terms reflect the relatively small effects which are attributable to respiration and other physiological activities. These effects can be extracted and utilized for analysis of respiration and other clinically-relevant parameters.

Once $\Delta mHbO2$ is calculated, completion of the CaO2 calculation requires determination of $\Delta V$ (Eqn. 5). This can be accomplished in numerous ways.

Thus, CaO2 is calculated in real-time by one of several similar algorithms entirely through noninvasive means. If the algorithm solving directly for $\Delta mHbO2$ is used, THb can be calculated using the SpO2 output from another device, such as the pulse oximeter, with the equation $$THb(g/dl) = CaO2(ml\ O2/dl)/[SpO2 \times 1.39(ml\ O2/g\ HbO2)]. \qquad (10)$$

Figure 1:
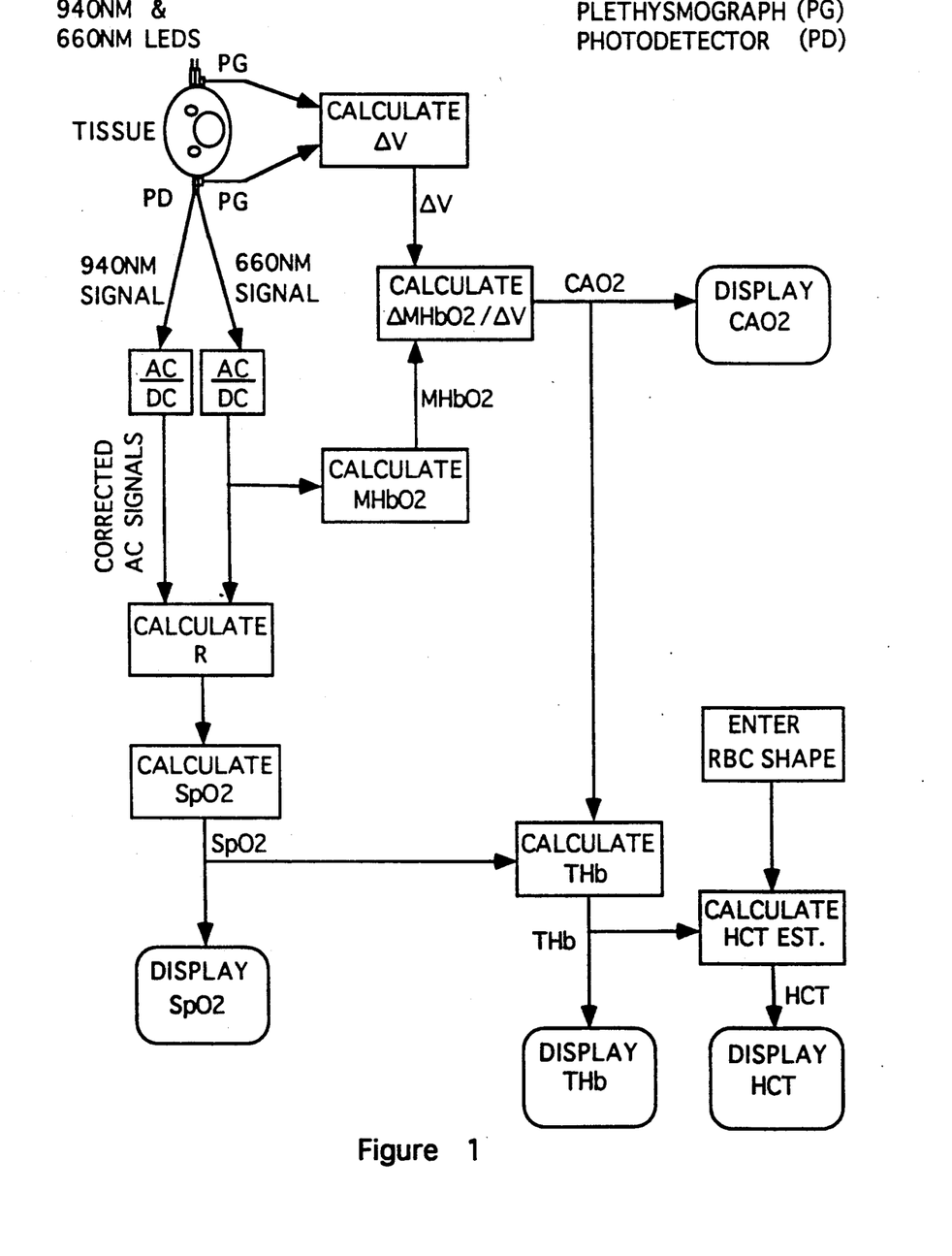
FIG. 1 is a schematic representation of one embodiment of the invention where HbO2 is measured directly and pulse oximeter is utilized.

Of course, if the light source from a pulse oximeter is used to obtain $\Delta mHbO2$, then SpO2 from that same pulse oximeter, or similar device, can be utilized (FIG. 1).

Hct can be estimated from either CaO2 or THb using additional calibration curves. Most commonly, Hct is well approximated by multiplying THb by a factor of three. For example, if a patient has a CaO2 = 20 ml O2/dl at SpO2 = 100% and a THb = 15 g/dl (i.e., 15 gram-percent), one can estimate that with normal red blood cell (RBC) morphology Hct is likely to be 45%. If THb is reduced, a proportional Hct change can be anticipated. If one has prior knowledge of RBC morphology, for example, that the RBC's are macrocytic or microcytic, then this can be entered into the monitor and an appropriate calibration curve used.

The claimed device comprises a small appliance that is easily attached to the patient. For example, the device can be attached onto the finger, earlobe, wrist, lips, nares, tongue, cheek, or some other site. The device further comprises a signal processing part that displays the results. The device displays CaO2, Hb, and an estimate of Hct continuously or intermittently. Theoretically, MetHb, and COHb can also be quantified.

Although SpO2 input to the device is required for calculation of THb with two of the algorithms, the device does not necessarily require incorporation into a pulse oximeter, or similar device, to determine THb. Instead, an SpO2 value can be obtained via the digital output port of a pulse oximeter, or similar device, and input into the proposed device. Thus, the device could be incorporated into a pulse oximeter (or similar device), as illustrated in FIG. 1, or operate as a unit distinct from it as diagrammed in FIGS. 2, 3 and 4.

Following are examples which illustrate procedures, including the best mode, for practicing the invention. These examples should not be construed as limiting. All percentages are by weight and all solvent mixture proportions are by volume unless otherwise noted.

EXAMPLE 1

The invention claimed here can be practiced with only one light source and a means of $\Delta V$ determination. Access to SpO2 output (obtained from any accurate source, such as a pulse oximeter) is required to calculate either THb and Hct, or CaO2, depending upon the algorithm chosen. In one embodiment, the novel device can be built into a pulse oximeter; no additional light source is required. The component that determines $\Delta V$ is also supplied. The measurement of changes in mHbO2 is then correlated to volume changes that are either passively measured or actively produced.

EXAMPLE 2

Figure 2:
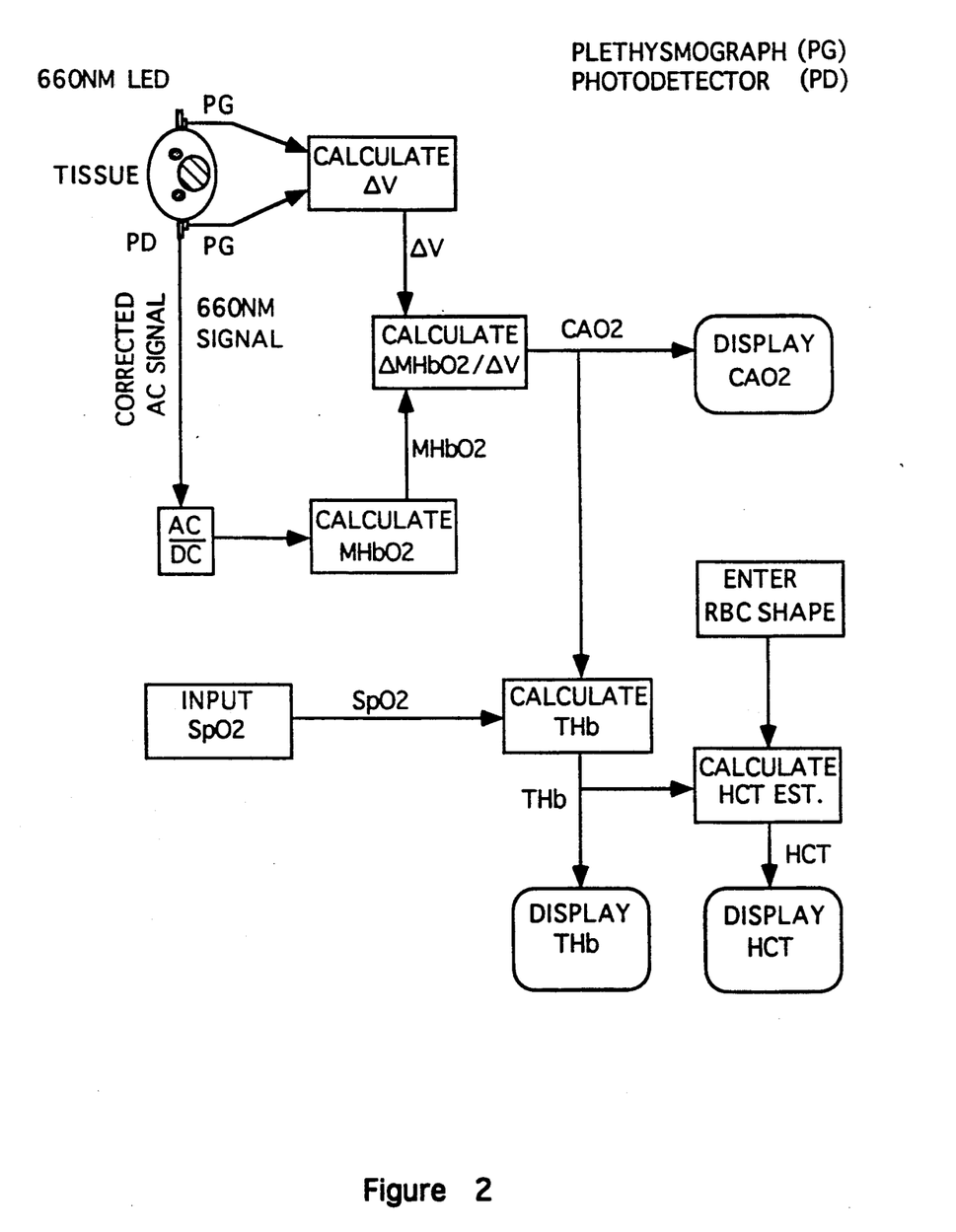
FIG. 2 is a schematic representation of one embodiment of the invention where HbO2 is measured directly and a pulse oximeter is not explicitly incorporated.
Figure 3:
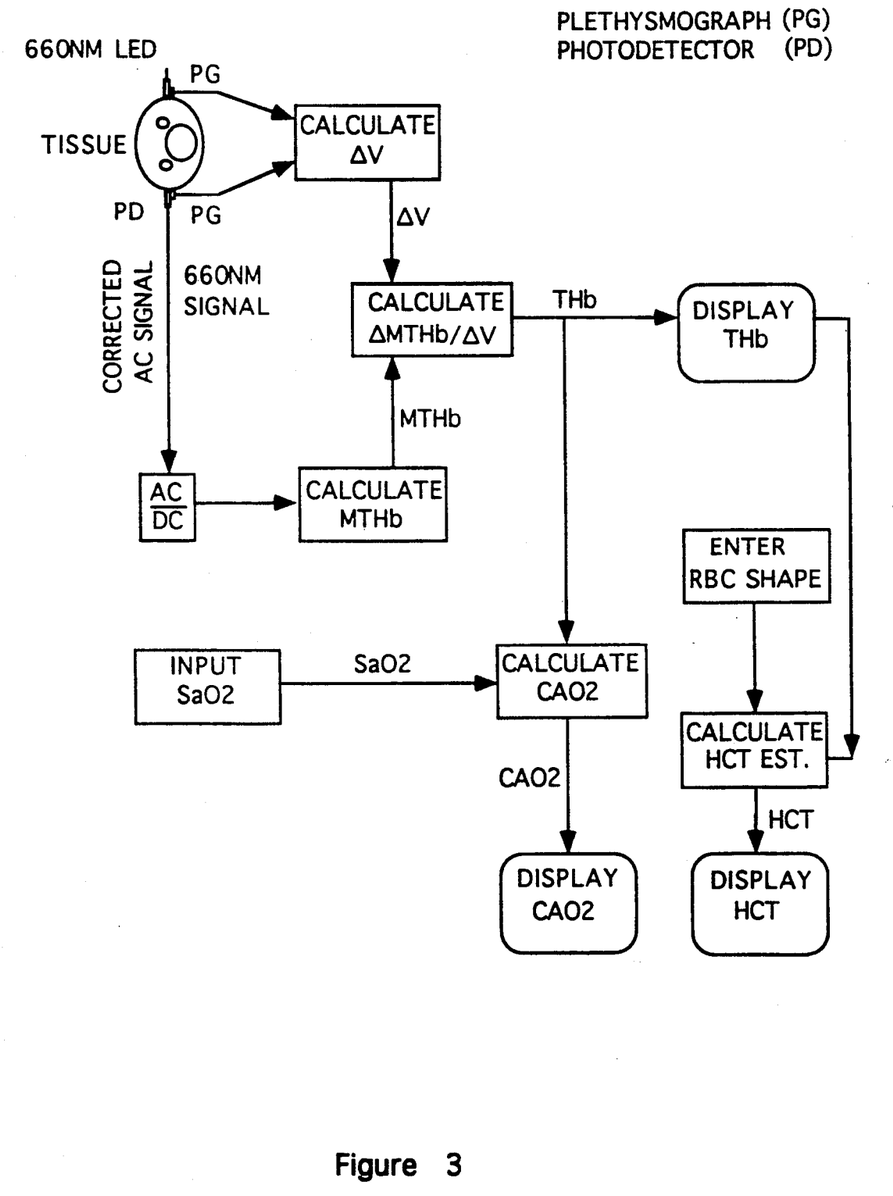
FIG. 3 is a schematic representation of one embodiment of the invention where THb is measured directly and a pulse oximeter is not explicitly incorporated.

Changes in the mass of oxyhemoglobin, total hemoglobin, and reduced hemoglobin molecules can be measured via absorption photometry using light having a wavelength from between about 400 nm and about 1100 nm. For example, a wavelength of about 660 nm can be used for direct HbO2 measurement (FIG. 2). Other wavelengths which can be utilized include 810 nm (direct THb determination, see FIG. 3) and 940 nm (direct RHb measurement). These wavelengths of light are sensitive to changes in mHbO2, mTHb, and mRHb, respectively.

The corrected AC signal can be extracted from a standard pulse oximeter. Alternatively, such a corrected AC signal could be readily obtained by a person skilled in the art utilizing standard equipment and photometric procedures. However, correction of the AC signal is not necessary in all applications. The AC or DC signal can be used in the algorithm where THb is measured directly (FIG. 4) using 810 nm light.

Figure 4:
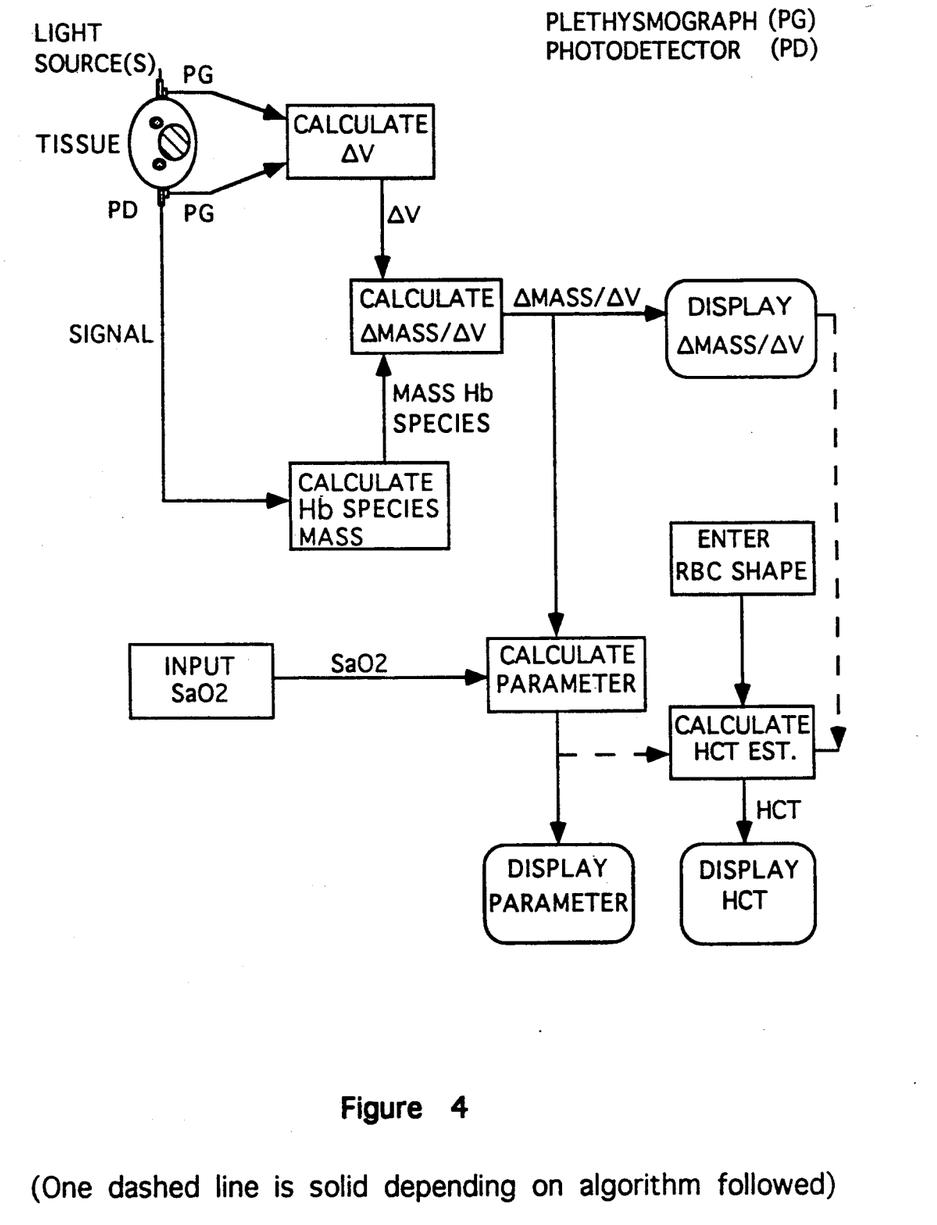
FIG. 4 is a schematic representation of one embodiment of the invention where desired hemoglobin species is/are measured and a pulse oximeter is not explicitly incorporated.

The desired DC or AC signal is then used to calculate ΔmHbO2. In the embodiment where mHbO2 is measured directly, for example, this can be done by generating a calibration curve which relates change of mHbO2 to changes in 660 nm corrected AC signal amplitude. ΔmHbO2 can be determined indirectly with the DC signal from an 810 nm light source. THb is measured directly and with SpO2, ΔmHbO2 is then calculated using equation (2).

There are a number of commercially available pulse oximeters which are capable of supplying the desired AC and/or DC signal. Additionally, these devices can be used to obtain accurate SpO2 input values. For example, the Nellcor N-100 (Nellcor, Inc., Hayward, CA) and Ohmeda 3700 (Ohmeda, Boulder, CO) pulse oximeters are accurate to within 7% of their displayed saturations (Cecil, W.T., K. J. Thorpe, E. E. Fibuch, and G. F. Tuohy [1988] J. Clin. Monit. 4(1):31-36). The Datascope ACCUSAT (Datascope Corp., Paramus, NJ) and the Ohmeda 3700 pulse oximeters display saturation within 2.4% of actual SaO2 (Mendelson, Y. J. C. Kent, A. Shahnarian, G. W. Welch, and R. M. Giasi [1988] J. Clin. Monit. 4(1):59-63). Regression analysis shows these products have high correlation coefficients with small standard error of estimate ($r=0.99$, $SEE=1.29\%$ and $r=0.99$, $SEE=1.72\%$ for the Datascope ACCUSAT and Ohmeda 3700, respectively).

EXAMPLE 3

Although only a single light source is needed in most adult patients, more than a single light source can also be employed. Indeed, additional light sources may be useful in determining CaO2 in circumstances where other light-absorbing hemoglobin species are present. Measurement of other light-absorbing blood constituents may also require additional light sources to optimize the measurement accuracy. Determination of the proper wavelength to be used for measuring various blood constituents is within the skill of those trained in this field.

EXAMPLE 4

Any type of energy which can be measured and used to quantitate blood constituents may be used to practice the subject invention. Thus, any form of electromagnetic radiation, sound wave, or magnetic property which can be used to trans-irradiate a body part can be utilized so long as the characteristics of the energy are altered by the relevant blood constituents and so long as these changes can be measured and correlated with changes in blood volume.

Furthermore, it is not critical that the energy be externally supplied. By measuring energetic and/or magnetic properties emitted from the tissue itself, it is possible to practice the invention. For example, by analyzing the magnetic properties attributable to the iron associated with hemoglobin and correlating these properties with changes in the blood volume, the relevant blood constituents can theoretically be quantified.

EXAMPLE 5

It is possible to measure volume changes directly using volume or pressure transduction. For example, a noninvasive blood pressure (NIBP) monitor generates an arterial pressure wave form using an air filled bladder around the finger. This commercially available device rapidly pressurizes and depressurizes the bladder to maintain the finger surrounded by the bladder at nearly constant volume during the pulse. The pressure changes in the bladder can be correlated to volume changes in the finger utilizing standard gas law calculations. These calculations take into account original bladder volume, gas temperature, change in bladder volume and compliance of the bladder.

EXAMPLE 6

A second approach for determining volume changes is to measure changes in the length of the light path between the light source and photodetector. Then the volume is approximated by modelling the light path. For example, this model can be a cylinder between emitter and detector with a cross-sectional area equal to the receptive field of the photodetector. When the length of this cylinder changes, such as occurs during pulsatile blood flow, the new volume and, hence, the volume change, are easily determined.

A variety of devices exist that transduce length with high precision. Sonomicrometers, strain gauges, Hall-effect transducers, optical interferometry, and electromagnetic field changes can all be utilized to measure small changes in length. Light intensity itself and light phase changes can also be used to measure distance changes.

EXAMPLE 7

Measurements or changes in volume can be made passively or actively. Passive measurement would involve, for example, measuring the actual finger expansion and contraction with each pulse. We have been able to show that finger volume does change with each pulse. The finger was placed into a closed rigid chamber (syringe plunger port) filled with an incompressible fluid (water). A pressure transducer (Datascope P3 Module interfaced with a Datascope 870 Monitor, Datascope Corp., Paramus, NJ) was primed with water and connected to the syringe tip. A pulsatile pressure wave form was obtained and reproduced. This provides evidence that the finger does indeed experience volume changes with blood pulsation.

This experiment also demonstrates the feasibility of one method of volume change determination. If the pulse amplitude, original finger volume, original chamber size, and compliance of the rigid vessel are known, the volume change in the finger can be determined. This change can be used to calculate the volume change between the LED and photodetector.

EXAMPLE 8

Measurement of actively produced volume changes can also be utilized. Active measurement results from compression and release of tissue at the measurement site by a known distance. If the light source and the photodetector are brought closer together by an external force, e.g., a motor, which produces a volume change in the receptive field, the same data can be obtained. This method requires some amount of HbO2 to be displaced from the receptive field.

This procedure can result in the measurement of larger changes in volume compared to passive measurements of volume change during a pulse. Measuring larger volume changes can advantageously reduce experimental error during measurement.

EXAMPLE 9

The device and method of the subject invention can be utilized in conjunction with life support systems and other medical instrumentations. For example, the subject invention can be used as a sensor for a continuous automatic feedback loop that is designed to maintain CaO2 and/or Hb or Hct. An infusion pump, ventilator, and/or anethesia machine can be controlled by the sensor. The sensor would enable the system to maintain levels of CaO2 and/or Hb/Hct at levels which are predetermined by the operator of the system.

EXAMPLE 10

The wavelength and source of light employed in the design of the invention can be optimized by those skilled in the art, depending on the particular application. Thus, if direct mHbO2 determination is desired, an approximately 660 nm light source can be utilized. If, however, direct mTHb determination is desired, a wavelength near the isobestic point of 805 nm (e.g., 810 nm) can be employed. If direct determination of RHb is sought, a light wavelength near 940 nm can be used. With any of these wavelengths, the remaining unknown parameters (THb and/or Hct and/or RHb and/or CaO2) can be determined indirectly with the addition of an accurate SpO2 value using the various formulae discussed above.

Furthermore, the light can be from an LED and/or laser source, such as a laser diode. The laser offers advantages over an LED because its emission spectra is much narrower, its power attenuation with increasing distance is small in comparison, its output is more directional and it is a more ideal beam. Thus, reproducibility and confidence are improved. These advantages allow for easier modeling and subsequent implementation of applications where the distance between light source and receiver changes.

If a laser source is utilized, the use of fiber-optic technology may also be employed. Fiber-optic cables allow the somewhat motion-, temperature-, and current-sensitive laser and detector elements to remain protected and remote from the patient, and also provide an extremely high degree of electrical isolation between the patient and the device.

EXAMPLE 11

Noise consists of the background light that enters the photovoltaic cell (PVC) and alters the signal output. Polarizing films can be employed to reduce the effects of background scattered light. This is achieved by placing a polarizing film in a known orientation between the emitter and tissue and another film in an identical orientation between the tissue and receiver. This configuration prevents randomly polarized light from entering the PVC. As a consequence, scattered light from the emitter, as well as ambient light that is rotated with respect to the orientation of the polarizing films, is filtered from the PVC input. All photoplethysmographic devices, including pulse oximeters, would benefit from this application.

The use of polarizing films in this fashion has the added advantage of essentially defining a volume of tissues of similar cross-sectional area to the PVC.

The volume's length is the linear distance between emitter and detector. Hence, volume determination is simplified.

EXAMPLE 12

"Active" volume determination requires a physical displacement of the emitter relative to the PVC. This displacement can be mechanically limited to a known distance. It can also be limited by the tissue pressure upon one of the device elements (i.e., the PVC or light source), or by a combination of pressure and displacement.

EXAMPLE 13

Light near the isobestic point of HbO2 and RHb (e.g., 810 nm) is absorbed essentially equally well by both species. Therefore, an AC signal representative of pulsatile arterial blood and a DC signal representative of both arterial and venous blood can be obtained. Since arterial and venous THb are the same, either the AC or DC signal can be utilized to determine THb. Input of SpO2 (which reflects arterial oxygen saturation) then allows arterial oxygen content (CaO2) to be calculated. If a DC signal is also obtained at 660 nm, a total (i.e., combined) arterial and venous oxygen content (CavO2) can be determined. Venous O2 content (CvO2) can then be calculated by subtracting CaO2 from CavO2. If one integrates over time (CaO2−CvO2), one can determine local O2 consumption.

EXAMPLE 14

The method of actively varying volume can be applied equally well to the new pulse oximeter technologies that employ reflectance or backscatter of light for their signals. If one varied the slab length, width, or depth from which they receive their signals, essentially a volume change would have been made and similar algorithms to those described above would apply. Therefore, SpO2, THb, HbO2, RHb, CaO2 and local oxygen consumption could each be determined using these new technologies.

EXAMPLE 15

The claimed device can also be used to determine interstitial fluid content, or state of hydration. Currently, there is no device which can quantitatively measure a patient's hydration status. Such a device would be beneficial in the clinical assessment of delirium, hypotension, tachycardia, and other medical conditions. Thus, it could be used in critical care settings (e.g., emergency rooms) and in chronic care settings (e.g., nursing homes).

The novel device of the subject invention operates by measuring changes in signal strength that occur after a rapid compression (or decompression) of a tissue. The tissue can be thought of as a two compartment system: the intravascular compartment that contains blood and the interstitial compartment that contains body water. By externally deforming the tissue, a hydrostatic pressure change is applied. Since the fluid cannot shift instantaneously between compartments, it shifts first within the compartment with the least resistance to flow. The interstitial fluid is impeded from making rapid shifts because it is trapped in tissue planes and held within the interstitial compartment by hydrophilic molecules. The blood within the intravascular compartment, however, is capable of making rapid shifts. Thus, upon rapid compression, blood would leave the compressed site almost immediately, and only subsequently does the interstitial water begin to leave the compressed region. Likewise, if the tissue was rapidly decompressed, blood would almost immediately refill the vasculature. Following this, the water would refill the interstitial compartment. The rate at which these shifts occur can be used as an indication of hydration status for any given blood pressure.

The measured signal varies with the mass of absorber (i.e., mass of HbO2, RHb, or THb, depending on the wavelength used) in the light path. As reasoned above, after rapid (de)compression, the signal can be expected to vary in a fashion that is related to hydration status.

EXAMPLE 16

It is possible to combine any of the various applications into a new application. For example, a backscatter oximeter may be used to determine mixed venous O2 content in the superficial jugular vein while CaO2 is determined at a peripheral site. Such a combination may provide a good solution to the Fick equation for cardiac output. Another example of a new application is to combine the algorithms that directly determine mTHb and mHbO2 by the new method and design an entirely new pulse oximeter based on measured vascular volume changes.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for noninvasively determining one or more of the following blood parameters: total hemoglobin, arterial oxygen content, and hematocrit, in an animal or human; said method comprising one or more of the following:
   (a) measuring changes in the mass of total hemoglobin in a specified portion of said human or animal, as a function of changes in blood volume in said specified portion of said animal or human to obtain a value for $\Delta THb/\Delta V$ and calculating at least one of the above parameters using known relationships between $\Delta THb/\Delta V$ and the parameter of interest;
   (b) measuring changes in mass of oxyhemoglobin in a specified portion of said animal or human as a function of changes in blood volume in said specified portion of said animal or human to obtain a value for $\Delta HbO2/\Delta V$ and calculating at least one of the above parameters using known relationships between $\Delta HbO2/\Delta V$ and the parameter of interest; and
   (c) measuring changes in mass of reduced hemoglobin in a specified portion of said animal or human as a function of changes in blood volume in said specified portion of said animal or human to obtain a value for $\Delta RHb/\Delta V$ and calculating at least one of the above parameters using known relationships between $\Delta RHb/\Delta V$ and the parameter of interest.

2. The method, according to claim 1, wherein said body part is selected from the group consisting of hands, fingers, feet, toes, ears, earlobes, nares, lips, and tongue.

3. The method, according to claim 1, wherein said volume change is measured by pressure transduction.

4. The method, according to claim 1, wherein said volume change is approximated by measuring changes in the length of a volume of known cross-sectional area.

5. The method, according to claim 4, wherein said length is measured by means selected from the group consisting of sonomicrometers, strain gauges, and optical interferometry.

6. The method, according to claim 1, wherein said volume change is determined by measuring the pulsatile pressure wave form obtained when a body part is immersed in an incompressible fluid.

7. The method, according to claim 6, wherein said incompressible fluid is water.

8. The method, according to claim 1, wherein said volume change is a passive volume change.

9. The method, according to claim 8, wherein said volume change is that which is caused by a natural pulse associated with heart beats and circulation.

10. The method, according to claim 1, wherein said volume change is actively induced by external means.

11. The method, according to claim 10, wherein said volume change is effected by a mechanically limited and known change in length of a volume of known cross-sectional area.

12. The method, according to claim 1, wherein said measuring of the changes in the mass of total hemoglobin, oxyhemoglobin, or reduced hemoglobin is accomplished by subjecting said specified body part to electromagnetic radiation of an appropriate wavelength.

13. The method, according to claim 2, wherein a first polarizing film is placed between a laser and the body portion to be subjected to said radiation, and a second polarizing film is placed between the body portion subjected to said radiation and a device for measurement of the attenuation of said radiation, said polarizing films being aligned such that radiation emitted by said laser and passing directly through said body portion will reach said measuring device.

14. The method, according to claim 12, wherein said wavelength is selected from the group consisting of approximately 660 nm, approximately 810 nm, and approximately 940 nm.

* * * * *

UNITED STATES PATENT AND TRADEMARK OFFICE
CERTIFICATE OF CORRECTION

PATENT NO.   :   5,101,825

DATED        :   April 7, 1992

INVENTOR(S)  :   Dietrich Gravenstein, et al.

It is certified that error appears in the above-identified patent and that said Letters Patent is hereby corrected as shown below:

Column 10  line 43: Delete "2" and insert --12--.

Signed and Sealed this

Fifteenth Day of June, 1993

Attest:

MICHAEL K. KIRK

Attesting Officer

Acting Commissioner of Patents and Trademarks